(12) United States Patent
Liang et al.

(10) Patent No.: US 9,562,236 B2
(45) Date of Patent: Feb. 7, 2017

(54) TRANSCRIPTION TERMINATORS

(75) Inventors: Delin Liang, Camarillo, CA (US); Nickolai Alexandrov, Thousand Oaks, CA (US); Yu-Ping Lu, Beijing (CN)

(73) Assignee: Ceres, Inc., Thousand Oaks, CA (US)

( * ) Notice: Subject to any disclaimer, the term of this patent is extended or adjusted under 35 U.S.C. 154(b) by 250 days.

(21) Appl. No.: 14/238,300

(22) PCT Filed: Aug. 10, 2012

(86) PCT No.: PCT/US2012/050300
§ 371 (c)(1),
(2), (4) Date: Jul. 9, 2014

(87) PCT Pub. No.: WO2013/025485
PCT Pub. Date: Feb. 21, 2013

(65) Prior Publication Data
US 2014/0345006 A1    Nov. 20, 2014

Related U.S. Application Data

(60) Provisional application No. 61/523,012, filed on Aug. 12, 2011.

(51) Int. Cl.
| | | |
|---|---|---|
| *A01H 5/00* | (2006.01) | |
| *C12N 15/82* | (2006.01) | |
| *C07K 14/415* | (2006.01) | |
| *C07H 21/04* | (2006.01) | |
| *C12N 15/00* | (2006.01) | |

(52) U.S. Cl.
CPC ......... *C12N 15/8218* (2013.01); *C07K 14/415* (2013.01); *C12N 15/8216* (2013.01)

(58) Field of Classification Search
None
See application file for complete search history.

(56) References Cited

U.S. PATENT DOCUMENTS

| | | | |
|---|---|---|---|
| 5,204,253 | A | 4/1993 | Sanford et al. |
| 5,538,880 | A | 7/1996 | Lundquist et al. |
| 6,013,863 | A | 1/2000 | Lundquist et al. |
| 6,329,571 | B1 | 12/2001 | Hiei |
| PP13,008 | P2 | 9/2002 | Walsh |
| PP14,743 | P2 | 5/2004 | Speichert et al. |
| PP15,193 | P2 | 9/2004 | Smith et al. |
| 6,906,244 | B2 | 6/2005 | Fischer et al. |
| PP16,176 | P3 | 1/2006 | Cosner et al. |
| 7,109,393 | B2 | 9/2006 | Gutterson et al. |
| 7,214,789 | B2 | 5/2007 | Pennell |
| PP18,161 | P2 | 10/2007 | Probst |
| 7,312,376 | B2 | 12/2007 | Apuya et al. |
| 7,378,571 | B2 | 5/2008 | Apuya et al. |
| 7,429,692 | B2 | 9/2008 | Dang |
| 2003/0217388 | A1 | 11/2003 | Feyereisen et al. |
| 2005/0223434 | A1 | 10/2005 | Alexandrov et al. |
| 2005/0229270 | A1 | 10/2005 | Fischer et al. |
| 2006/0010518 | A1 | 1/2006 | Feldmann et al. |
| 2006/0015970 | A1 | 1/2006 | Pennell et al. |
| 2006/0021083 | A1 | 1/2006 | Cook et al. |
| 2006/0041952 | A1 | 2/2006 | Cook |
| 2006/0057724 | A1 | 3/2006 | Alexandrov et al. |
| 2006/0112454 | A1 | 5/2006 | Christensen et al. |
| 2006/0134786 | A1 | 6/2006 | Feldmann |
| 2006/0143729 | A1 | 6/2006 | Alexandrov et al. |
| 2006/0150285 | A1 | 7/2006 | Nadzan et al. |
| 2006/0168696 | A1 | 7/2006 | Feldmann et al. |
| 2006/0195943 | A1 | 8/2006 | Feldmann et al. |
| 2006/0260004 | A1 | 11/2006 | Fang et al. |
| 2006/0294622 | A1 | 12/2006 | Sosa et al. |
| 2007/0006335 | A1 | 1/2007 | Cook et al. |
| 2007/0006345 | A1 | 1/2007 | Alexandrov et al. |
| 2007/0006346 | A1 | 1/2007 | Alexandrov et al. |
| 2007/0039067 | A1 | 2/2007 | Feldmann et al. |
| 2007/0061914 | A1 | 3/2007 | Feldmann |
| 2007/0083953 | A1 | 4/2007 | Christensen et al. |
| 2007/0094750 | A1 | 4/2007 | Jofuku |
| 2007/0101460 | A1 | 5/2007 | Feldman et al. |
| 2007/0174936 | A1 | 7/2007 | Alexandrov et al. |
| 2007/0192907 | A1 | 8/2007 | Alexandrov et al. |
| 2007/0214517 | A1 | 9/2007 | Alexandrov et al. |
| 2007/0277269 | A1 | 11/2007 | Alexandrov et al. |
| 2008/0072340 | A1 | 3/2008 | Troukhan et al. |
| 2008/0131581 | A1 | 6/2008 | Schneeberger et al. |

(Continued)

FOREIGN PATENT DOCUMENTS

| | | |
|---|---|---|
| WO | WO 02/00900 | 1/2002 |
| WO | WO 2005/098007 | 10/2005 |

(Continued)

OTHER PUBLICATIONS

Lin et al., GenEmbl Database, Acc. No. AC006201, Direct submission, Mar. 11, 2002.*
U.S. Appl. No. 60/505,689, Cook et al., filed Sep. 23, 2003.
U.S. Appl. No. 60/518,075, Pennell et al., filed Nov. 6, 2003.
U.S. Appl. No. 60/544,771, Cook et al., filed Feb. 13, 2004.
U.S. Appl. No. 60/558,869, Cook et al., filed Apr. 1, 2004.
U.S. Appl. No. 60/583,609, Alexandrov et al., filed Jun. 30, 2004.
U.S. Appl. No. 60/583,691, Alexandrov et al., filed Jun. 30, 2004.
U.S. Appl. No. 60/612,891, Kwok et al., filed Sep. 23, 2004.
U.S. Appl. No. 60/619,181, Medrano, filed Oct. 14, 2004.
U.S. Appl. No. 60/637,140, Feldmann, filed Dec. 16, 2004.
U.S. Appl. No. 60/757,544, Dang, filed Jan. 9, 2006.
U.S. Appl. No. 60/776,307, Kwok et al., filed Feb. 24, 2006.
U.S. Appl. No. 61/407,280, Apuya, filed Oct. 27, 2010.
Abler and Scandalios, "Isolation and characterization of a genomic sequence encoding the maize Cat3 catalase gene," Plant Mol. Biol., Sep. 1993, 22:1031-1038.

(Continued)

*Primary Examiner* — Phuong Bui

(57) ABSTRACT

This document provides methods and materials related to transcription terminators. For example, methods and materials related to transcription terminators and nucleic acid molecules (e.g., vectors and constructs) that contain a nucleic acid sequence that encodes a polypeptide operably linked to a transcription terminator are provided. In addition, plants, plant cells, and plant seeds having a nucleic acid sequence that encodes a polypeptide operably linked to a transcription terminator are provided.

13 Claims, 1 Drawing Sheet

(56) References Cited

U.S. PATENT DOCUMENTS

| | | |
|---|---|---|
| 2008/0184386 A1 | 7/2008 | Cao et al. |
| 2011/0014706 A2 | 1/2011 | Cao et al. |

FOREIGN PATENT DOCUMENTS

| | | |
|---|---|---|
| WO | WO 2006/005023 | 1/2006 |
| WO | WO 2006/034479 | 3/2006 |
| WO | WO 2006/036864 | 4/2006 |
| WO | WO 2007/044988 | 4/2007 |
| WO | WO 2007/055826 | 5/2007 |
| WO | WO 2007/120989 | 10/2007 |
| WO | WO 2010/033564 | 3/2010 |
| WO | WO 2011/011412 | 1/2011 |
| WO | WO 2011/044254 | 4/2011 |
| WO | WO 2011/140329 | 11/2011 |

OTHER PUBLICATIONS

Ausubel et al., Short Protocols in Molecular Biology, 3rd Ed., John Wiley & Sons, Inc., 1995, 26 pages.
Baerson et al., "Developmental regulation of an acyl carrier protein gene promoter in vegetative and reproductive tissues," Plant Mol. Biol., 1993, 22(2):255-267.
Bevan et al., "Binary Agrobacterium vectors for plant transformation," Nucl Acid Res, 1984, 12(22):8711-8721.
Braga et al., "Expression of the Cry 1Ab Protein in Genetically Modified Sugarcane for the Control of *Diatraea saccharalis* (*Lepidoptera*: crambidae)," Journal of New Seeds, 2003, 5:209-221.
Brown (ed.), Molecular Biology Labfax, Academic Press, 1991, 12 pages.
Bustos et al., "Regulation of B-Glucuronidase Expression in Transgenic Tobacco Plants by an A/T-Rich, cis-Acting Sequence Found Upstream of a French Bean B-Phaseolin Gene," The Plant Cell, 1989, 1(9):839-853.
Cerdan et al., "A 146 bp fragment of the tobacco Lhcbl*2 promoter confers very-low-fluence and high-irradiance responses of phytochrome to a minimal CaMV 35S promoter," Plant Mol. Biol., 1997, 33:245-255.
Chen and Winans, "Controlled expression of the transcriptional activator gene virG in Agrobacterium tumefaciens by using the *Escherichia coli* lac promoter," J. Bacteriol, 1991, 173(3):1139-1144.
Chen et al., "Functional analysis of regulatory elements in a plant embryo-specific gene," Proc. Natl. Acad. Sci. USA, 1986, 83:8560-8564.
Chenna et al., "Multiple sequence alignment with the Clustal series of programs," Nucleic Acids Res., 2003, 31(13):3497-500.
Conceicao, "A cotyledon regulatory region is responsible for the different spatial expression patterns of *Arabidopsis* 2S albumin genes," The Plant Journal, 1994, 5:493-505.
Conkling et al., "Isolation of Transcriptionally Regulated Root-Specific Genes from Tobacco," Plant Physiol., 1990, 93:1203-1211.
Dai et al., "RF2b, a rice bZIP transcription activator, interacts with RF2a and is involved in symptom development of rice tungro disease," Proc. Natl. Acad. Sci. USA, 2004, 101(2):687-692.
Fejes et al., "A 268 bp upstream sequence mediates the circadian clock-regulated transcription of the wheat Cab-1 gene in transgenic plants," Plant Mol. Biol., 1990, 15:921-932.
Fraley et al., CRC Crit. Rev. Plant. Sci, 4:145 (1985).
Fromm et al., "An octopine synthase enhancer element directs tissue-specific expression and binds ASF-1, a factor from tobacco nuclear extracts," The Plant Cell, 1989, 1:977-984.
GenBank Accession No. AF096096 GI: 4185500, Genes controlling fertilization-independent seed development in *Arabidopsis thaliana*, 1999, 2 pages.
GenBank Accession No. AF129516 GI: 4567094, Mutations in FIE, a WD polycomb group gene, allow endosperm development without fertilization, 1999, 2 pages.
Genbank Accession No. AV534030 GI: 8694313, A large scale analysis of cDNA in *Arabidopsis thaliana*. Generation of 12,028 non-redundant expressed sequence tags from normalized and size-selected cDNA libraries, dated May 12, 2010, 1 page.
GenBank Accession No. L05934 GI: 168436, Isolation and characterization of a genomic sequence encoding the maize Cat3 catalase gene, 1993, 3 pages.
GenBank Accession No. U93215 GI: 20198323, *Arabidopsis thaliana* chromosome 2 BAC T6B20 genomic sequence, 2002, 42 pages.
GenBank Accession No. U11256 GI: 1086462, Structure, organization and expression of the metallothionein gene family in *Arabidopsis*, Nov. 30, 1995, 2 pages.
Green et al., "Binding site requirements for pea nuclear protein factor GT-1 correlate with sequences required for light-dependent transcriptional activation of the rbcS-3A gene," The EMBO J., 1988, 7:4035-4044.
Hansen et al., "Constitutive expression of the virulence genes improves the efficiency of plant transformation by Agrobacterium," Proc. Natl. Acad. Sci. USA, 1994, 91(16):7603-7607.
Hoekema, "The Binary Plant Vector System," Offsetdrukkerij Kanters B. V, Alblasserdam, Chapter V, 1985, 9 pages.
Holsters et al., "Transfection and transformation of Agrobacterium tumefaciens," Mol Gen Genet, 1978, 163(2):181-187.
Hong et al., "Promoter sequences from two different *Brassica napus* tapetal oleosin-like genes direct tapetal expression of beta-glucuronidase in transgenic *Brassica* plants," Plant Mol. Biol., 1997, 34(3):549-555.
Hwang et al, "Aleurone- and embryo-specific expression of the β-glucuronidase gene controlled by the barley Chi26 and Ltp1 promoters in transgenic rice" Plant Cell Rep., 2001, 20(7):647-654.
International Preliminary Report on Patentability in International Application No. PCT/US2012/050300, dated Feb. 18, 2014, 9 pages.
International Search Report and Written Opinion in International Application No. PCT/US2012/050300, dated Sep. 19, 2012, 17 pages.
Jordano et al., "A sunflower helianthinin gene upstream sequence ensemble contains an enhancer and sites of nuclear protein interaction," Plant Cell, 1989, 1(9):855-866.
Kasuga et al., "Improving plant drought, salt, and freezing tolerance by gene transfer of a single stress-inducible transcription factor," Nature Biotech, 1999, 17(3):287-291.
Keller and Baumgartner, "Vascular-specific expression of the bean GRP 1.8 gene is negatively regulated," Plant Cell, 1991, 3(10):1051-1061.
Lam et al., "Site-specific mutations alter in vitro factor binding and change promoter expression pattern in transgenic plants," Proc. Natl. Acad. Sci. USA, 1989, 86(20):7890-7894.
Luan et al., "A rice cab gene promoter contains separate cis-acting elements that regulate expression in dicot and monocot plants," Plant Cell, 1992, 4(8):971-981.
Lubberstedt et al., "Promoters from genes for plastid proteins possess regions with different sensitivities toward red and blue light," Plant Physiol., 1994, 104(3):997-1006.
Matsuoka et al., "Tissue-specific light-regulated expression directed by the promoter of a C4 gene, maize pyruvate,orthophosphate dikinase, in a C3 plant, rice," Proc. Natl. Acad. Sci. USA, 1993, 90(20):9586-9590.
Medberry et al., "The Commelina yellow mottle virus promoter is a strong promoter in vascular and reproductive tissues," Plant Cell, 1992, 4(2):185-192.
Meier et al., "Elicitor-Inducible and Constitutive in Vivo DNA Footprints Indicate Novel cis-Acting Elements in the Promoter of a Parsley Gene Encoding Pathogenesis-Related Protein 1," Plant Cell, 1991, 3:309-316.
Miki et al., "Procedures for Introducing Foreign DNA into Plants" in Methods in Plant Molecular Biology and Biotechnology: pp. 67-88 (1993).
Moloney et al., "High efficiency transformation of*Brassica napus* using Agrobacterium vectors," Plant Cell Reports, 1989, 8(4):238-242.
Mozo & Hooykaas, "Electroporation of megaplasmids into Agrobacterium," Plant Mol. Biol., 1991, 16(5): 917-918.

(56) References Cited

OTHER PUBLICATIONS

PCR Primer: A Laboratory Manual, Dieffenbach, C. & Dveksler, G., Eds., Cold Spring Harbor Laboratory Press, 1995.

Riggs et al., "Cotyledon nuclear proteins bind to DNA fragments harboring regulatory elements of phytohemagglutinin genes," Plant Cell, 1989, 1(6):609-621.

Sheridan, "The mac1 gene: controlling the commitment to the meiotic pathway in maize," Genetics, 1996, 142(3):1009-1020.

Slocombe et al., "Temporal and Tissue-Specific Regulation of a *Brassica napus* Stearoyl-Acyl Carrier Protein Desaturase Gene," Plant Physiol., 104(4):1167-1176 (1994).

Truernit et al., "The promoter of the *Arabidopsis thaliana* SUC2 sucrose-H+ symporter gene directs expression of beta-glucuronidase to the phloem: evidence for phloem loading and unloading by SUC2," Planta, 1995, 196(3):564-570.

Urao, "Molecular cloning and characterization of a gene that encodes a MYC-related protein in *Arabidopsis*," Plant Mol. Biol., 1996, 32(3):571-576.

Watson et al., "New cloning vehicles for transformation of higher plants," EMBO J., 1985, 4(2):277-284.

Yamamoto et al., "The promoter of a pine photosynthetic gene allows expression of a beta-glucuronidase reporter gene in transgenic rice plants in a light-independent but tissue-specific manner," Plant Cell Physiol., 1994, 35(5):773-778.

Zhang et al., "DNA sequences that activate isocitrate lyase gene expression during late embryogenesis and during postgerminative growth," Plant Physiology, 1996, 110(4):1069-1079.

Zheng et al., "SPK1 is an essential S-phase-specific gene of *Saccharomyces cerevisiae* that encodes a nuclear serine/threonine/tyrosine kinase," Mol. Cell Biol., 1993, 13(9):5829-5842.

\* cited by examiner

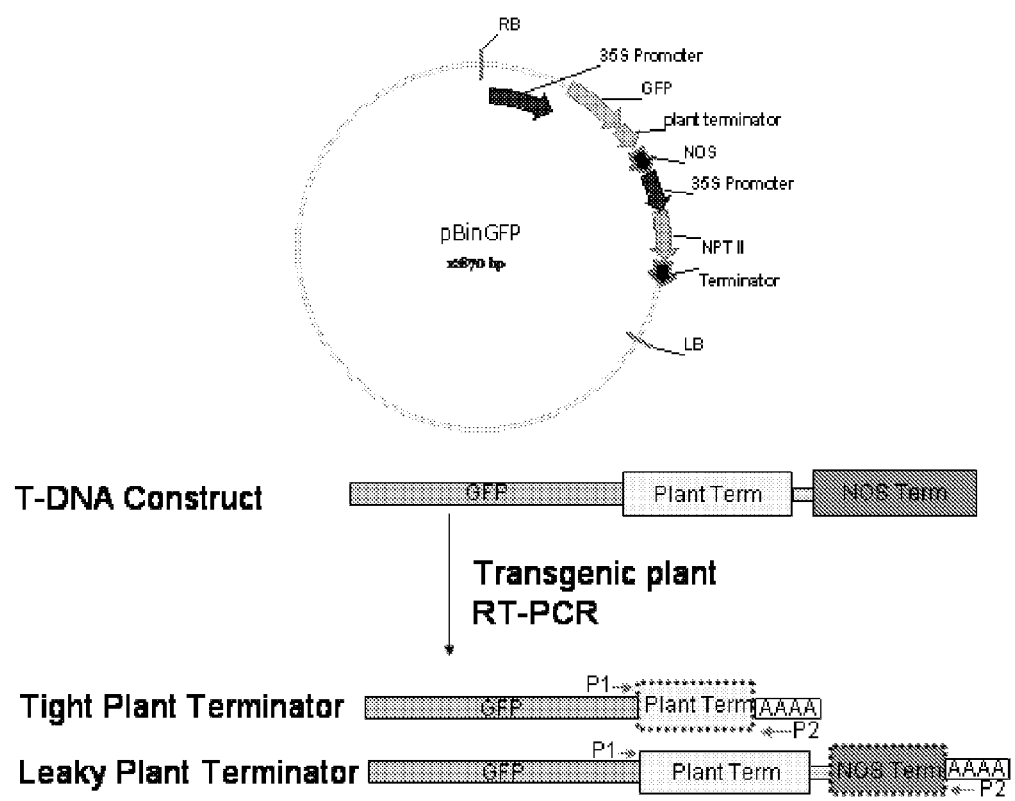

SEQUENCE LISTING

```
<160> NUMBER OF SEQ ID NOS: 5

<210> SEQ ID NO 1
<211> LENGTH: 300
<212> TYPE: DNA
<213> ORGANISM: Arabidopsis thaliana

<400> SEQUENCE: 1
tgcttatatg taataattgg ctgattttc cggtagtttt gccggcgacg ttggtctttc      60
tcttcttctg tgtgtgtttt tatggtttgg tcattaagat atctctgcaa agttttatct   120
ttgtgacttt attaatccta agactattat gggtttgtat taaagtttgc ttctttcttg   180
ctcactacac aattaagatt caagcccatt gtctctctgg ttataaagct taaacataca   240
agaacagaca ataatgaaat tacacgagat agaactgata taatacacaa gtgttgttgt   300

<210> SEQ ID NO 2
<211> LENGTH: 288
<212> TYPE: DNA
<213> ORGANISM: Arabidopsis thaliana

<400> SEQUENCE: 2
agttaaaaga gataaacttt gtttctcttg ttttctatgt ttcaagtttt gttgtctgtg      60
tttccttttg aacctcattc tgaaatccta aaagattttt atgataaacc tttctctctt   120
ctcgaaaagc ttatgttatt cacattgcat actctcaata cgcaaagttt tcattttgta   180
catatgaaaa ttatgtaaga acaacgtaac caattctcgt gatcgttaaa gtggtagttg   240
aattgcagat tttcatcgaa acagcagccc gccgcattgc tatcacaa                288

<210> SEQ ID NO 3
<211> LENGTH: 300
<212> TYPE: DNA
<213> ORGANISM: Arabidopsis thaliana
```

```
<400> SEQUENCE: 3
tatcccccat ctttgatttt atccttgtt tttctgcttt tttcttcttt cttgggtttt        60
aatttccgga cttaacgttt gttttccggt ttgcgagaca tattctatcg gattctcaac       120
tgtctgatga aataaatatg taatgttcta taagtctttc aatttgatat gcatatcaac       180
aaaaagaaaa taggacaatg cggctacaaa tatgaaattt acaagtttaa gaaccatgag       240
tcgctaaaga aatcattaag aaaattagtt tcacattcaa ttcttgtcac atgattaacg       300

<210> SEQ ID NO 4
<211> LENGTH: 240
<212> TYPE: DNA
<213> ORGANISM: Arabidopsis thaliana

<400> SEQUENCE: 4
tgctgctctt ataattatat attttggtt attgttgttg tcaagctttg gtaaaacttg        60
atggatacat gttacatttg tttatgaaga agctctttc ttggtagatg aaaaaattgg       120
gaatcctcac taatcagtaa ctctgcatct actgtttat ccatgccctc cattgcttca       180
tatatctctt catataattt ttttgtgaaa cttgctttag tgttgagaaa atgaacgaga       240

<210> SEQ ID NO 5
<211> LENGTH: 300
<212> TYPE: DNA
<213> ORGANISM: Arabidopsis thaliana

<400> SEQUENCE: 5
ttctccatcg gaactctgtt cccggaactg ggttcttgat cggaggtggc ggagctactt        60
tgcacctatt ttgcttttga attgttatca attttgaacc tatttggaga ttcggttata       120
tgatgtgatt ttccgaggat attctctctt tttttgttgc gtgtatcaca ttcgaattca       180
gtctcttgga taacttgtgg aaaaacttat aacttcaaga aaaaccttat aaacacttac       240
aacttcaaca aaatatcgta actgccattg tagattgttt ttactccgat tcgcttgagc       300
```

TRANSCRIPTION TERMINATORS

CROSS REFERENCE TO RELATED APPLICATIONS

This application is a National Stage Application under 35 U.S.C. §371 and claims the benefit of International Application No. PCT/US2012/050300, filed Aug. 10, 2012, which claims the benefit of U.S. Provisional Application Ser. No. 61/523,012, filed Aug. 12, 2011. The disclosures of the prior applications are considered part of (and are incorporated by reference in) the disclosure of this application.

BACKGROUND

1. Technical Field

This document relates to methods and materials involved in terminating transcription. For example, this document provides transcription terminators that can be used to terminate transcription of exogenous nucleic acids inserted into plant cells.

2. Background Information

One of the goals of modern agriculture is to produce plants with advantageous phenotypes, such as disease resistance, pest resistance, cold and drought resistance, increased yields, and improved nutrition. Generating plants with these enhanced characteristics can be done using modern genetic engineering techniques, including transforming plants with transgenes involved in these processes. Developing engineered plants with enhanced characteristics can lead to increased crop yields as well as yield stability under various environmental conditions.

SUMMARY

This document provides methods and materials related to transcription terminators. For example, this document provides transcription terminators and nucleic acid molecules (e.g., vectors) containing a nucleic acid sequence that encodes a polypeptide operably linked to a transcription terminator. Such transcription terminators can be used to terminate transcription of an exogenous nucleic acid. This document also provides plants, plant cells, and plant seeds containing nucleic acid molecules having a nucleic acid sequence that encodes a polypeptide operably linked to a transcription terminator. Having the ability to use the transcription terminators provided herein to terminate transcription of a nucleic acid inserted into a plant cell can prevent inappropriate transcription of downstream genes, allow for the efficient recycling of RNA polymerases, and reduce the likelihood of gene silencing (i.e., inactivation) when inserting multiple nucleic acid molecules. The transcription terminators provided herein are derived from a plant species, not a bacterial species, thereby reducing the difficulty of obtaining regulatory approval.

In general, one aspect of this document features an isolated transcription terminator consisting of a nucleotide sequence having at least 99% identity to the nucleotide sequence selected from the group consisting of SEQ ID NO:1, SEQ ID NO:2, SEQ ID NO:3, SEQ ID NO:4, and SEQ ID NO:5. The isolated transcription terminator can have at least 99% identity to the sequence set forth in SEQ ID NO:1. The isolated transcription terminator can comprise the sequence set forth in SEQ ID NO:1. The isolated transcription terminator can have at least 99% identity to the sequence set forth in SEQ ID NO:2. The isolated transcription terminator can comprise the sequence set forth in SEQ ID NO:2. The isolated transcription terminator can have at least 99% identity to the sequence set forth in SEQ ID NO:3. The isolated transcription terminator can comprise the sequence set forth in SEQ ID NO:3. The isolated transcription terminator can have at least 99% identity to the sequence set forth in SEQ ID NO:4. The isolated transcription terminator can comprise the sequence set forth in SEQ ID NO:4. The isolated transcription terminator can have at least 99% identity to the sequence set forth in SEQ ID NO:5. The isolated transcription terminator can comprise the sequence set forth in SEQ ID NO:5.

In another aspect, this document features an isolated nucleic acid molecule comprising, or consisting essentially of, a nucleotide sequence encoding a polypeptide operably linked to a transcription terminator, wherein the nucleotide sequence is heterologous to the transcription terminator, and wherein the transcription terminator comprises a nucleotide sequence having at least 99% identity to the sequence set forth in SEQ ID NO:1, SEQ ID NO:2, SEQ ID NO:3, SEQ ID NO:4, or SEQ ID NO:5. The isolated nucleic acid molecule can be a vector. The transcription terminator can comprise a nucleotide sequence having at least 99% identity to the sequence set forth in SEQ ID NO:1. The transcription terminator can comprise the sequence set forth in SEQ ID NO:1. The transcription terminator can comprise a nucleotide sequence having at least 99% identity to the sequence set forth in SEQ ID NO:2. The transcription terminator can comprise the sequence set forth in SEQ ID NO:2. The transcription terminator can comprise a nucleotide sequence having at least 99% identity to the sequence set forth in SEQ ID NO:3. The transcription terminator can comprise the sequence set forth in SEQ ID NO:3. The transcription terminator can comprise a nucleotide sequence having at least 99% identity to the sequence set forth in SEQ ID NO:4. The transcription terminator can comprise the sequence set forth in SEQ ID NO:4. The transcription terminator can comprise a nucleotide sequence having at least 99% identity to the sequence set forth in SEQ ID NO:5. The transcription terminator can comprise the sequence set forth in SEQ ID NO:5.

In another aspect, this document features a plant cell comprising a nucleotide sequence encoding a polypeptide operably linked to a transcription terminator, wherein the nucleotide sequence is heterologous to the transcription terminator, and wherein the transcription terminator comprises a nucleotide sequence having at least 99% identity to the sequence set forth in SEQ ID NO:1, SEQ ID NO:2, SEQ ID NO:3, SEQ ID NO:4, or SEQ ID NO:5. The plant cell can be a canola, corn, cotton, miscanthus, rice, rye, sorghum, soybean, sugar beet, sunflower, switchgrass, or wheat plant cell. The transcription terminator can comprise a nucleotide sequence having at least 99% identity to the sequence set forth in SEQ ID NO:1. The transcription terminator can comprise the sequence set forth in SEQ ID NO:1. The transcription terminator can comprise a nucleotide sequence having at least 99% identity to the sequence set forth in SEQ ID NO:2. The transcription terminator can comprise the sequence set forth in SEQ ID NO:2. The transcription terminator can comprise a nucleotide sequence having at least 99% identity to the sequence set forth in SEQ ID NO:3. The transcription terminator can comprise the sequence set forth in SEQ ID NO:3. The transcription terminator can comprise a nucleotide sequence having at least 99% identity to the sequence set forth in SEQ ID NO:4. The transcription terminator can comprise the sequence set forth in SEQ ID NO:4. The transcription terminator can comprise a nucleotide sequence having at least 99% identity to the sequence set forth in SEQ ID NO:5. The transcription terminator can comprise the sequence set forth in SEQ ID NO:5. The nucleotide sequence and the transcription terminator can be located on a nucleic acid molecule not integrated into the genome of the plant cell. The nucleotide sequence and the transcription terminator can be located within the genome of the plant cell.

In another aspect, this document features a plant comprising a plant cell comprising a nucleotide sequence encoding a polypeptide operably linked to a transcription terminator, wherein the nucleotide sequence is heterologous to the transcription terminator, and wherein the transcription terminator comprises a nucleotide sequence having at least 99% identity to the sequence set forth in SEQ ID NO:1, SEQ ID NO:2, SEQ ID NO:3, SEQ ID NO:4, or SEQ ID NO:5. The plant can be a canola, corn, cotton, miscanthus, rice, rye, sorghum, soybean, sugar beet, sunflower, switchgrass, or wheat plant. The transcription terminator can comprise a nucleotide sequence having at least 99% identity to the sequence set forth in SEQ ID NO:1. The transcription terminator can comprise the sequence set forth in SEQ ID NO:1. The transcription terminator can comprise a nucleotide sequence having at least 99% identity to the sequence set forth in SEQ ID NO:2. The transcription terminator can comprise the sequence set forth in SEQ ID NO:2. The transcription terminator can comprise a nucleotide sequence having at least 99% identity to the sequence set forth in SEQ ID NO:3. The transcription terminator can comprise the sequence set forth in SEQ ID NO:3. The transcription terminator can comprise a nucleotide sequence having at least 99% identity to the sequence set forth in SEQ ID NO:4. The transcription terminator can comprise the sequence set forth in SEQ ID NO:4. The transcription terminator can comprise a nucleotide sequence having at least 99% identity to the sequence set forth in SEQ ID NO:5. The transcription terminator can comprise the sequence set forth in SEQ ID NO:5.

In another aspect, this document features a seed comprising a nucleotide sequence encoding a polypeptide operably linked to a transcription terminator, wherein the nucleotide sequence is heterologous to the transcription terminator, and wherein the transcription terminator comprises a nucleotide sequence having at least 99% identity to the sequence set forth in SEQ ID NO:1, SEQ ID NO:2, SEQ ID NO:3, SEQ ID NO:4, or SEQ ID NO:5. The seed can be a canola, corn, cotton, miscanthus, rice, rye, sorghum, soybean, sugar beet, sunflower, switchgrass, or wheat seed. The transcription terminator can comprise a nucleotide sequence having at least 99% identity to the sequence set forth in SEQ ID NO:1. The transcription terminator can comprise the sequence set forth in SEQ ID NO:1. The transcription terminator can comprise a nucleotide sequence having at least 99% identity to the sequence set forth in SEQ ID NO:2. The transcription terminator can comprise the sequence set forth in SEQ ID NO:2. The transcription terminator can comprise a nucleotide sequence having at least 99% identity to the sequence set forth in SEQ ID NO:3. The transcription terminator can comprise the sequence set forth in SEQ ID NO:3. The transcription terminator can comprise a nucleotide sequence having at least 99% identity to the sequence set forth in SEQ ID NO:4. The transcription terminator can comprise the sequence set forth in SEQ ID NO:4. The transcription terminator can comprise a nucleotide sequence having at least 99% identity to the sequence set forth in SEQ ID NO:5. The transcription terminator can comprise the sequence set forth in SEQ ID NO:5.

In another aspect, this document features a vector comprising, or consisting essentially of, a nucleic acid molecule comprising a nucleotide sequence encoding a polypeptide operably linked to a transcription terminator, wherein the nucleotide sequence is heterologous to the transcription terminator, and wherein the transcription terminator comprises a nucleotide sequence having at least 99% identity to the sequence set forth in SEQ ID NO:1, SEQ ID NO:2, SEQ ID NO:3, SEQ ID NO:4, or SEQ ID NO:5.

In another aspect, this document features an isolated nucleic acid molecule comprising, or consisting essentially of, in a 5' to 3' direction, at least a portion of a nucleic acid sequence of a plant to be silenced followed by an antisense terminator sequence followed by a loop sequence followed by a transcription terminator, and wherein the transcription terminator comprises a nucleotide sequence having at least 99% identity to the sequence set forth in SEQ ID NO:1, SEQ ID NO:2, SEQ ID NO:3, SEQ ID NO:4, or SEQ ID NO:5. The portion of the nucleic acid sequence of a plant to be silenced can be between about 50 and about 150 nucleotides in length. The antisense terminator sequence can comprise the reverse complement sequence of the sequence set forth in SEQ ID NO:1, 2, 3, 4, or 5. The loop sequence can be between about 60 and about 70 nucleotides in length.

In another aspect, this document features a method for reducing expression of an endogenous plant polypeptide within a plant. The method comprises, or consists essentially of, inserting a nucleic acid molecule into the plant, wherein the nucleic acid molecule comprises, or consists essentially of, in a 5' to 3' direction, at least a portion of a nucleic acid sequence encoding the plant polypeptide followed by an antisense terminator sequence followed by a loop sequence followed by a transcription terminator, and wherein the transcription terminator comprises a nucleotide sequence having at least 99% identity to the sequence set forth in SEQ ID NO:1, SEQ ID NO:2, SEQ ID NO:3, SEQ ID NO:4, or SEQ ID NO:5. The portion of the nucleic acid sequence of a plant to be silenced can be between about 50 and about 150 nucleotides in length. The antisense terminator sequence can comprise the reverse complement sequence of the sequence set forth in SEQ ID NO:1, 2, 3, 4, or 5. The loop sequence can be between about 60 and about 70 nucleotides in length.

In another aspect, this document features use of a transcription terminator to produce a nucleic acid that comprises a nucleic acid sequence encoding a polypeptide and that terminates transcription of the nucleic acid sequence downstream of the nucleic acid sequence, wherein the transcription terminator is heterologous to the nucleic acid sequence and is located downstream of the nucleic acid sequence, and wherein the transcription terminator comprises a nucleotide sequence having at least 99% identity to the sequence set forth in SEQ ID NO:1, SEQ ID NO:2, SEQ ID NO:3, SEQ ID NO:4, or SEQ ID NO:5. The transcription terminator can comprise a nucleotide sequence having at least 99% identity to the sequence set forth in SEQ ID NO:1. The transcription terminator can comprise the sequence set forth in SEQ ID NO:1. The transcription terminator can comprise a nucleotide sequence having at least 99% identity to the sequence set forth in SEQ ID NO:2. The transcription terminator can comprise the sequence set forth in SEQ ID NO:2. The transcription terminator can comprise a nucleotide sequence having at least 99% identity to the sequence set forth in SEQ ID NO:3. The transcription terminator can comprise the sequence set forth in SEQ ID NO:3. The transcription terminator can comprise a nucleotide sequence having at least 99% identity to the sequence set forth in SEQ ID NO:4. The transcription terminator can comprise the sequence set forth in SEQ ID NO:4. The transcription terminator can comprise a nucleotide sequence having at least 99% identity to the sequence set forth in SEQ ID NO:5. The transcription terminator can comprise the sequence set forth in SEQ ID NO:5.

In another aspect, this document features use of a transcription terminator to produce a nucleic acid for terminating transcription of a nucleic acid sequence encoding a polypeptide within a plant, wherein the nucleic acid comprises the transcription terminator and the nucleic acid sequence, wherein the transcription terminator is heterologous to the nucleic acid sequence and is located downstream of the nucleic acid sequence, and wherein the transcription terminator comprises a nucleotide sequence having at least 99% identity to the sequence set forth in SEQ ID NO:1, SEQ ID NO:2, SEQ ID NO:3, SEQ ID NO:4, or SEQ ID NO:5. The plant can be a canola, corn, cotton, miscanthus, rice, rye, sorghum, soybean, sugar beet, sunflower, switchgrass, or wheat plant. The transcription terminator can comprise a nucleotide sequence having at least 99% identity to the sequence set forth in SEQ ID NO:1. The transcription terminator can comprise the sequence set forth in SEQ ID NO:1. The transcription terminator can comprise a nucleotide sequence having at least 99% identity to the sequence set forth in SEQ ID NO:2. The transcription terminator can comprise the sequence set forth in SEQ ID NO:2. The transcription terminator can comprise a nucleotide sequence having at least 99% identity to the sequence set forth in SEQ ID NO:3. The transcription terminator can comprise the sequence set forth in SEQ ID NO:3. The transcription terminator can comprise a nucleotide sequence having at least 99% identity to the sequence set forth in SEQ ID NO:4. The transcription terminator can comprise the sequence set forth in SEQ ID NO:4. The transcription terminator can comprise a nucleotide sequence having at least 99% identity to the sequence set forth in SEQ ID NO:5. The transcription terminator can comprise the sequence set forth in SEQ ID NO:5.

In another aspect, this document features use of a transcription terminator to produce a plant comprising an exogenous nucleic acid, the exogenous nucleic acid comprising a nucleic acid sequence that encodes a polypeptide and that terminates transcription of the nucleic acid sequence downstream of the nucleic acid sequence, wherein the transcription terminator is heterologous to the nucleic acid sequence and is located downstream of the nucleic acid sequence, and wherein the transcription terminator comprises a nucleotide sequence having at least 99% identity to the sequence set forth in SEQ ID NO:1, SEQ ID NO:2, SEQ ID NO:3, SEQ ID NO:4, or SEQ ID NO:5. The plant can be a canola, corn, cotton, miscanthus, rice, rye, sorghum, soybean, sugar beet, sunflower, switchgrass, or wheat plant. The transcription terminator can comprise a nucleotide sequence having at least 99% identity to the sequence set forth in SEQ ID NO:1. The transcription terminator can comprise the sequence set forth in SEQ ID NO:1. The transcription terminator can comprise a nucleotide sequence having at least 99% identity to the sequence set forth in SEQ ID NO:2. The transcription terminator can comprise the sequence set forth in SEQ ID NO:2. The transcription terminator can comprise a nucleotide sequence having at least 99% identity to the sequence set forth in SEQ ID NO:3. The transcription terminator can comprise the sequence set forth in SEQ ID NO:3. The transcription terminator can comprise a nucleotide sequence having at least 99% identity to the sequence set forth in SEQ ID NO:4. The transcription terminator can comprise the sequence set forth in SEQ ID NO:4. The transcription terminator can comprise a nucleotide sequence having at least 99% identity to the sequence set forth in SEQ ID NO:5. The transcription terminator can comprise the sequence set forth in SEQ ID NO:5.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting. In some instances, features of the invention may consist essentially of that feature rather than comprise that feature. Section headings are provided merely for convenience. The word "comprising" in the claims may be replaced by "consisting essentially of" or with "consisting of," according to standard practice in patent law.

DESCRIPTION OF THE DRAWINGS

FIG. 1 depicts a vector that can be used to confirm the effectiveness of a transcription terminator to terminate transcription.

DETAILED DESCRIPTION

This document provides methods and materials related to transcription terminators. For example, this document provides transcription terminators and nucleic acid molecules (e.g., vectors) containing a nucleic acid sequence that encodes a polypeptide operably linked to a transcription terminator.

In general, transcription terminators can be positioned within the 3' end region of a transgene and provide for the efficient termination of transcription and addition of a polyA tail to the RNA transcript for synthesis of mature mRNA. As described herein, a transcription terminator having the sequence set forth in SEQ ID NOs: 1, 2, 3, 4, or 5 can be used to terminate transcription of an upstream nucleic acid that encodes a polypeptide.

DEFINITIONS

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid also can be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Nucleic acid" and "polynucleotide" are used interchangeably herein, and refer to both RNA and DNA, including cDNA, genomic DNA, synthetic DNA, and DNA or RNA containing nucleic acid analogs. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region (e.g., a transcription terminator provided herein) within a nucleic acid sequence relative to the coding region of a nucleic acid, such that the regulatory region effects the stability or transcription of that nucleic acid. For example, a regulatory region can be a promoter or enhancer positioned upstream of the coding region of a gene that increases transcription of the gene. A promoter or enhancer can be positioned as much as about 5,000 nucleotides upstream of the translation initiation site or about 2,000 nucleotides upstream of the transcription start site. For example, to operably link a coding sequence and a regulatory region, the translation initiation site of the translational reading frame of the coding sequence is typically positioned between one and about 50 nucleotides downstream of the regulatory region. A regulatory region also can be a transcription terminator that is positioned downstream of the coding region of a nucleic acid. For example, a transcription terminator can be positioned within the 3'UTR of a gene and can trigger termination of transcription of that gene.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation or rate, or stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, transcription terminator sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

"Transgene" as used herein refers to any nucleic acid sequence that is introduced into the genome of a cell by experimental manipulation. A transgene may be an "endogenous DNA sequence," or a "heterologous DNA sequence" (i.e., "foreign DNA"). The term "endogenous DNA sequence" refers to a nucleotide sequence that is naturally found in the cell into which it is transformed so long as it does not contain some modification (e.g., a point mutation, the presence of a selectable marker gene, etc.) relative to the naturally-occurring sequence. The term "heterologous DNA sequence" refers to a nucleotide sequence that is operably linked to, or is manipulated to become operably linked to, a nucleic acid sequence to which it is not operably linked in nature, or to which it is operably linked at a different location in nature. Heterologous DNA is not endogenous to the cell into which it is transformed, but has been obtained from another cell. Heterologous DNA also includes an endogenous DNA sequence which contains some modification. Generally, although not necessary, heterologous DNA encodes RNA and proteins that are not normally produced by the cell into which it is transformed. Examples of heterologous DNA include reporter genes, transcriptional and translational regulatory sequences, transcription terminators, selectable marker proteins (e.g., proteins which confer drug resistance), etc.

"Vector" refers to a replicon, such as a plasmid (e.g., T-DNA), phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

Transcription Terminators

The transcription terminators provided herein can be used to facilitate the cessation of transcription of a transcript (e.g., an mRNA transcript). Examples of transcription terminators include, without limitation, transcription terminators having the nucleic acid sequence set forth in SEQ ID NO:1, 2, 3, 4, or 5. In some cases, a transcription terminator provided herein can have a nucleic acid sequence that has at least about 70% (e.g., at least about 75%, 80%, 85%, 90%, 95%, 97%, 98%, 99%, or 100%) sequence identity to the nucleic acid sequence set forth in SEQ ID NO:1, 2, 3, 4, or 5. For example, a transcription terminator provided herein can have the sequence set forth in SEQ ID NO:1, 2, 3, 4, or 5 with one, two, three, four, five, six, seven, eight, nine, ten, or more nucleotide additions, deletions, substitutions, or combinations thereof.

Percent sequence identity refers to the degree of sequence identity between any given reference sequence, e.g., SEQ ID NO:1 or portion thereof, and a candidate sequence. A candidate sequence typically has a length that is from 80% to 200% of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid relative to a reference nucleic acid can be determined as follows. A reference sequence (e.g., a nucleic acid sequence) is aligned to one or more candidate sequences using the computer program ClustalW (version 1.83, default parameters), which allows alignments of nucleic acid sequences to be carried out across their entire length (global alignment). Chema et al., *Nucleic Acids Res.*, 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. The ClustalW output is a sequence alignment that reflects the relationship between sequences. ClustalW can be run, for example, at the Baylor College of Medicine Search Launcher site on the World Wide Web (searchlauncher.bcm.tmc.edu/multi-align/multi-align.html) and at the European Bioinformatics Institute site on the World Wide Web (ebi.ac.uk/clustalw). To determine percent identity of a candidate nucleic acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a transcription terminator can be obtained using DNA synthesis or polymerase chain reaction (PCR) techniques. PCR refers to a procedure or technique in which target nucleic acids are amplified from a nucleic acid template, including DNA and RNA. For example, PCR can be used to obtain nucleic acid copies of the sequence set forth in SEQ ID NO:1, 2, 3, 4, or 5. Various PCR methods are described, for example, in *PCR Primer: A Laboratory Manual*, Dieffenbach, C. & Dveksler, G., Eds., Cold Spring Harbor Laboratory Press, 1995. Generally, sequence information from the ends of the region of interest or beyond is employed to design oligonucleotide primers that are identical or similar in sequence to opposite strands of the template to be amplified.

Various PCR strategies also are available by which site-specific nucleotide sequence modifications can be introduced into a template nucleic acid. The methods previously mentioned to calculate percent identity can be used along with PCR to create variants of template nucleic acids. For example, 1, 2, 3, 4, 5, 10, 20, 30 or more nucleotide alterations can be introduced into the sequence set forth in SEQ ID NO:1, 2, 3, 4, or 5. In some cases, a transcription terminator provided herein can be obtained using amplification techniques (e.g., PCR) designed to amplify sequences from a metallothionein 2b gene, a ribosomal protein L8 gene, a aribulose-bisphosphate carboxylase gene, a cytochrome b6f complex gene, or a elongation factor 1 alpha plant gene. In some cases, transcription terminators can be obtained from other plant genes, plant genes that are not from *Arabidopsis thaliana*, or from genes from non-plant organisms. For example, a transcription terminator can be obtained from the elongation factor 1 alpha gene of a sorghum plant.

A transcription terminator can be tested to confirm its effectiveness for terminating transcription in plant cells using, for example, methods similar to those described in Example 2. For example, a transcription terminator can be inserted downstream of a reporter gene and upstream of a known transcription terminator (e.g., a NOS transcription terminator) to form a construct that can be transformed into plant cells. After a growth period, transcripts can be isolated and sequenced to determine whether termination occurred within the sequence of the transcription terminator being assessed or outside that sequence (e.g., within the known transcription terminator) (FIG. 1).

In some cases, a transcription terminator provided herein can be used to terminate transcription of a transgene in a plant having two or more transgenes. In some cases, one or more of the transcription terminators provided herein can be used to terminate transcription of a transgene in a plant containing multiple different transgenes in a manner where transcription of each transgene is terminated by different transcription terminators. For example, transcription of a first transgene within a plant can be terminated using a transcription terminator having the sequence set forth in SEQ ID NO:1 and transcription of a second transgene within that plant can be terminated using a transcription terminator having the sequence set forth in SEQ ID NO:2. The use of a different transcription terminator for each transgene within a plant can minimize the risk of triggering silencing of each transgene, i.e. inadvertent cross-silencing, which may occur when the same transcription terminator is used for multiple transgenes.

The expression of a desired sequence can be reduced using RNA interference or gene silencing techniques. In some cases, a transcription terminator provided herein can be used in methods and materials for inducing RNA interference or gene silencing. For example, an isolated nucleic acid molecule can be designed to include, in a 5' to 3' direction, an introduced nucleic acid sequence, which typically corresponds to a plant endogenously expressed sequence or to a pathogen sequence, and which may be in sense or antisense orientation, followed by an antisense terminator sequence, followed by a loop sequence, and followed by the sense sequence of the transcription terminator.

The introduced sequence need not be full length relative to either the primary transcription product or fully processed mRNA intended to be silenced. Generally, higher identity can be used to compensate for the use of a shorter sequence. In some embodiments, the targeting sequence is from a coding region, a 5' untranslated region, or a 3' untranslated region of the gene targeted for downregulation. In some embodiments, the introduced sequence can include a premature stop codon that inhibits translation of the expressed sequence. The introduced sequence need not have the same intron or exon pattern as the natural gene, and identity to non-coding segments may be effective. An introduced sequence can have a length of at least about 25 nucleotides, sometimes a sequence length of about 25 to about 50 nucleotides, sometimes a sequence length of about 50 to about 100 nucleotides, sometimes a sequence length of about 150 to about 200 nucleotides, sometimes a sequence length of about 200 to about 500, and sometimes a sequence length of about 500 to about 1000 or more nucleotides, up to a molecule that corresponds in size to a full length gene targeted for silencing.

Any appropriate antisense terminator sequences can be used in combination with a corresponding transcription terminator provided herein to induce RNA interference or gene silencing within a plant. In general, an antisense terminator sequence refers to a nucleic acid sequence that is the reverse compliment of a transcription terminator sequence (i.e., sense terminator sequence). For example, an antisense terminator sequence can have a sequence that is the reverse compliment of a transcription terminator provided herein. As those of skill in the art appreciate, the antisense terminator sequence need not encompass the entire length of the sense sequence, as long as they maintain the ability to form a double stranded RNA stem structure. Antisense and sense transcription terminator sequences can be included in the same nucleic acid molecule and can be separated by a linker sequence (e.g., a loop sequence). A single-stranded sense transcription terminator DNA or RNA molecule can hybridize with its corresponding single-stranded antisense transcription terminator DNA or RNA molecule to form a double-stranded inverted repeat. Examples of antisense terminator sequences include, without limitation, the reverse compliment of SEQ ID NO:1, 2, 3, 4, or 5. In some cases, an antisense terminator sequences can be positioned 3' of the nucleic acid sequence of a plant to be silenced (e.g., between about 1 to about 100 nucleotides 3' of the nucleic acid sequence of a plant to be silenced) and 5' of a loop sequence.

Any appropriate loop sequence can be used in combination with a transcription terminator provided herein to induce RNA interference or gene silencing within a plant. In general, a loop sequence (i.e., stem loop or hairpin loop) refers to a sequence in which two regions within a single DNA or RNA molecule that are reverse compliments of each other are separated by a non-complimentary region, such that the complimentary regions hybridize and form a "stem," while the non-complimentary region forms a "loop." In some cases, a loop sequence can be about 15 to about 200 nucleotides in length, more preferably between 20 and 100 nucleotides in length, and may be between 60 and 70 nucleotides in length, and positioned 3' of an antisense terminator sequence and 5' of a transcription terminator provided herein. In some cases, a loop sequence can be about 67 nucleotides in length. Examples of vectors and nucleic acid molecules that can be designed to include a transcription terminator provided herein for inducing RNA interference or gene silencing include, without limitation, those vectors and nucleic acid molecules described in U.S. Pat. No. 7,109,393.

Nucleic Acid Molecules

This document also provides nucleic acid molecules having a nucleic acid sequence encoding a polypeptide operably linked to a transcription terminator. As provided herein, the polypeptide encoded by the nucleic acid sequence can be, without limitation, a reporter polypeptide, an enzyme polypeptide, a receptor polypeptide, a ligand polypeptide, a membrane polypeptide, a structural polypeptide, or a nuclear polypeptide. In some cases, the polypeptide can be a plant polypeptide. For example, the polypeptide can be a polypeptide that naturally occurs in corn, sorghum, sunflower, switchgrass, miscanthus, rice, rye, or wheat plants. In some cases, the polypeptide can be a non-plant polypeptide. For example, the polypeptide can be a polypeptide that naturally occurs in a non-plant organism (e.g., a bacterial organism). In some cases, the polypeptide can be an endogenous polypeptide with respect to a plant, plant cell, or plant seed that is constructed to contain the nucleic acid that encodes that endogenous polypeptide. For example, the polypeptide can be a polypeptide that is naturally found within the plant in which a nucleic acid sequence encoding the polypeptide is inserted. In some cases, the polypeptide can be an exogenous polypeptide with respect to a plant, plant cell, or plant seed that is constructed to contain the nucleic acid that encodes that exogenous polypeptide. For example, the polypeptide can be a polypeptide that is not naturally found within the plant in which a nucleic acid sequence encoding the polypeptide is inserted. Examples of exogenous nucleic acid sequences that can be used in the methods described herein include, but are not limited to, sequences encoding genes or fragments thereof that modulate cold tolerance, frost tolerance, heat tolerance, drought tolerance, water used efficiency, nitrogen use efficiency, pest resistance, herbicide resistance, biomass, chemical composition, plant architecture, biopower conversion properties, and/or biofuel conversion properties. In particular, exemplary sequences are described in the following applications which are incorporated herein by reference in their entirety: WO2010/033564, WO2011/011412, PCT/US2011/035345, WO2011/044254, U.S. 61/407,280, US20080131581, US20080072340, US20070277269, US20070214517, US 20070192907, US 20070174936, US 20070101460, US 20070094750, US20070083953, US 20070061914, US20070039067, US20070006346, US20070006345, US20060294622, US20060195943, US20060168696, US20060150285, US20060143729, US20060134786, US20060112454, US20060057724, US20060010518, US20050229270, US20050223434, and US20030217388.

In some cases, nucleic acid molecules having a nucleic acid sequence encoding a polypeptide operably linked to a transcription terminator provided herein can be in the form of a vector. In addition to the nucleic acid sequence encoding a polypeptide and the transcription terminator, a vector can contain a larger sequence that serves as the backbone of the vector. Suitable vector backbones include, for example, those routinely used in the art such as plasmids, T-DNAs, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen® (Madison, Wis.), Clontech® (Palo Alto, Calif.), Stratagene® (La Jolla, Calif.), and Invitrogen/Life Technologies® (Carlsbad, Calif.).

In some cases, a vector provided herein can include, for example, an origin of replication, a scaffold attachment region (SARs), and/or a marker. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, glufosinate, chlorsulfuron or phosphinothricin). In addition, an expression vector can include a tag sequence designed to facilitate manipulation or detection (e.g., purification or localization) of an expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, Conn.) sequences typically are expressed as a fusion with the encoded polypeptide. Such tags can be inserted anywhere within the polypeptide, including at either the carboxyl or amino terminus.

In some cases, a nucleic acid molecule provided herein can be configured as a binary vector system commonly used for transgenesis in plants. Such binary vectors can include (in addition to the disarmed T-DNA with its border sequences), prokaryotic sequences for replication both in *Agrobacterium* and *E. coli*. It is an advantage of *Agrobacterium*-mediated transformation that in general only the DNA flanked by the borders is transferred into the genome and that preferentially only one copy is inserted. Descriptions of *Agrobacterium* vector systems and methods for *Agrobacterium*-mediated gene transfer are known in the art. See Miki et al., "Procedures for Introducing Foreign DNA into Plants" in *Methods In Plant Molecular Biology And Biotechnology*: pp. 67-88 (1993); Moloney et al., *Plant Cell Reports* 8:238-242 (1989). The use of T-DNA for the transformation of plant cells has been studied and described intensively. See Fraley et al., *CRC Crit. Rev. Plant. Sci*, 4:145 (1985). Various binary vectors are known, some of which are commercially available such as, for example, pBIN19 (Clontech Laboratories, Inc. USA).

For *Agrobacterium*-mediated transformation, a screening construct may be integrated into a screening vector or a screening construct may consist of specific plasmids, such as shuttle or intermediate vectors, or binary vectors. Binary vectors are generally preferable over other vector systems. Binary vectors are capable of replication both in *E. coli* and in *Agrobacterium*. They may comprise, for example, a selection marker gene and a linker or polylinker flanked by the right and left T-DNA border sequence. They can be transferred directly into *Agrobacterium*. See Holsters et al., *Mol Gen Genet*, 163:181-187 (1978). The selection marker gene permits the selection of transformed *Agrobacteria* and is, for example, the NPT 11 gene, which confers resistance to kanamycin. An *Agrobacterium* transformed in this way can be used for transforming plant cells. The use of T-DNA for transforming plant cells has been studied and described intensively. See Hoekema, "The Binary Plant Vector System," Offsetdrukkerij Kanters B. V, Alblasserdam, Chapter V (1985).

Common binary vectors are based on "broad host range" plasmids like pRK252, pTJS75, or vectors derived from the P-type plasmid RK2. Most of these vectors are derivatives of pBIN19. Various binary vectors are known, some of which are commercially available such as, for example, pBI101.2 or pBIN19 (Clontech Laboratories, Inc. USA). Additional vectors were improved with regard to size and handling (e.g. pPZP). See Watson et al., *EMBO J* 4(2):277-284 (1985); Bevan et al., *Nucl Acid Res* 12, 8711-8720 (1984). Improved vector systems also are described in WO 02/00900.

In some cases, the *Agrobacterium* strain used to transform the plant tissue pre-cultured with the plant phenolic compound contains an octopine-type Ti-plasmid, preferably disarmed, such as pAL4404. Generally, when using octopine-type Ti-plasmids or helper plasmids, it is preferred that the virF gene be deleted or inactivated. In some cases, particular *Agrobacterium* strains can be used to further increase the transformation efficiency, such as *Agrobacterium* strains wherein the vir gene expression and/or induction thereof is altered due to the presence of mutant or chimeric virA or virG genes. See Chen & Winans *J. Bacteriol.* 173: 1139-1144 (1991); Hansen et al., *Proc. Natl. Acad. Sci. USA* 91:7603-7607 (1994)

A binary vector or any other vector can be modified by common DNA recombination techniques, multiplied in *E. coli*, and introduced into *Agrobacterium* by electroporation or other transformation techniques. See Mozo & Hooykaas, *Plant Mol. Biol.* 16: 917-918 (1991). *Agrobacterium* can be grown and used as described in the art. The vector comprising *Agrobacterium* strain may, for example, be grown for three days on YP medium (5 g/L yeast extract, 10 g/L peptone, 5 g/L Nail, 15 g/L agar, pH 6.8) supplemented with the appropriate antibiotic (e.g., 50 mg/L spectinomycin). Bacteria can be collected with a loop from the solid medium and resuspended.

After constructing a vector, the vector can be propagated in a host cell to synthesize nucleic acid molecules for the generation of a polynucleotide. Vectors, often referred to as "shuttle vectors," are capable of replicating in at least two unrelated expression systems. To facilitate such replication, the vector should can at least two origins of replication, one effective in each replication system. Typically, shuttle vectors are capable of replicating in a eukaryotic system and a prokaryotic system. This enables detection of protein expression in eukaryotic hosts, the "expression cell type," and the amplification of the vector in the prokaryotic hosts, the "amplification cell type." As an illustration, one origin of replication can be derived from SV40, while another origin of replication can be derived from pBR322. Those of skill in the art know of numerous suitable origins of replication.

After constructing a vector, the vector is typically propagated in a host cell. Vector propagation can be conveniently carried out in a prokaryotic host cell, such as *E. coli* or *Bacillus subtilus*. Suitable strains of *E. coli* include BL21 (DE3), BL21 (DE3)pLysS, BL21(DE3) pLysE, DB2, DB3.1, DH1, DH4I, DH5, DH5I, DH5IF, DH5IMCR, DH10B, DH10B/p3, DH11S, C600, HB101, JM101, JM105, JM109, JM110, K38, RR1, Y1088, Y1089, CSH18, ER1451, and ER1647 (See, e.g., Brown (ed.), Molecular Biology Labfax, Academic Press (1991)). Suitable strains of *Bacillus subtilus* include BR151, YB886, M1119, M1120, and B170. Standard techniques for propagating vectors in prokaryotic hosts are well-known to those of skill in the art. See Ausubel et al., Short Protocols in Molecular Biology, $3^{rd}$ Ed., John Wiley & Sons, Inc. (1995).

The nucleic acid molecules and vectors provided herein as well as constructs having a nucleic acid sequence encoding a polypeptide operably linked to a transcription terminator can be constructed to include any appropriate additional regulatory region. Such molecules, vectors, and constructs having a nucleic acid sequence encoding a polypeptide operably linked to a transcription terminator can be inserted into plant cells as described herein. The choice of regulatory regions to be included can depend upon several factors, including, but not limited to, efficiency, selectability, inducibility, desired expression level, and cell- or tissue-preferential expression. The expression of a coding sequence can be modulated by appropriately selecting and positioning regulatory regions such as promoters and enhancers relative to the coding sequence.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996).

Examples of various classes of regulatory regions are described below. Some of the regulatory regions indicated below as well as additional regulatory regions are described in more detail in U.S. Patent Application Ser. Nos. 60/505,689; 60/518,075; 60/544,771; 60/558,869; 60/583,691; 60/619,181; 60/637,140; 60/757,544; 60/776,307; Ser. Nos. 10/957,569; 11/058,689; 11/172,703; 11/208,308; 11/274,890; 60/583,609; 60/612,891; Ser. Nos. 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid molecules, vectors, and constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter can be excluded from the category of broadly expressing promoters.

Root-active promoters confer transcription in root tissue, e.g., root endodermis, root epidermis, or root vascular tissues. In some cases, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990), and the tobacco RD2 promoter.

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and CryIA(b) and CryIA(c) (Braga et al., *Journal of New Seeds*, 5:209-221 (2003)).

In some cases, promoters that drive transcription in maturing endosperm can be used as described herein. Transcription from a maturing endosperm promoter typically begins after fertilization and occurs primarily in endosperm tissue during seed development and is typically highest during the cellularization phase. Suitable examples are promoters that are active predominantly in maturing endosperm, although promoters that are also active in other tissues can sometimes be used. Non-limiting examples of maturing endosperm promoters that can be included in the nucleic acid molecules, vectors, and constructs provided herein include the napin promoter, the Arcelin-5 promoter, the phaseolin promoter (Bustos et al., *Plant Cell*, 1(9):839-853 (1989)), the soybean trypsin inhibitor promoter (Riggs et al., *Plant Cell*, 1(6): 609-621 (1989)), the ACP promoter (Baerson et al., *Plant Mol. Biol.*, 22(2):255-267 (1993)), the stearoyl-ACP desaturase promoter (Slocombe et al., *Plant Physiol.*, 104(4):167-176 (1994)), the soybean α' subunit of β-conglycinin promoter (Chen et al., *Proc. Natl. Acad. Sci. USA*, 83:8560-8564 (1986)), the oleosin promoter (Hong et al., *Plant Mol. Biol.*, 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene, the beta-amylase promoter, and the barley hordein promoter. See Zheng et al., *Mol. Cell Biol.*, 13:5829-5842 (1993). Other maturing endosperm promoters that can be used include the YP0092, PT0676, and PT0708 promoters.

Promoters that are active in ovary tissues such as the ovule wall and mesocarp can be used, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

To achieve expression in embryo sac/early endosperm, regulatory regions can be used that are active in polar nuclei and/or the central cell, or in precursors to polar nuclei, but not in egg cells or precursors to egg cells. Examples of suitable promoters are those that are capable of driving expression only or predominantly in polar nuclei or precursors thereto and/or the central cell. A pattern of transcription that extends from polar nuclei into early endosperm development also can be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao, *Plant Mol. Biol.,* 32:571-57 (1996); Conceicao, *Plant,* 5:493-505 (1994)); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan, *Genetics,* 142:1009-1020 (1996)); maize Cat3 (see, GenBank No. L05934; Abler, *Plant Mol. Biol.,* 22:10131-1038 (1993)). Other promoters include the following *Arabidopsis* promoters: YP0039, YP0101, YP0102, YP0110, YP0117, YP0119, YP0137, DME, YP0285, and YP0212. Other promoters that may be used as described herein include the following rice promoters: p530c10, pOsFIE2-2, pOsMEA, pOsYp102, and pOsYp285.

Regulatory regions that preferentially drive transcription in zygotic cells following fertilization can provide embryo-preferential expression. Examples of suitable promoters are those promoters that preferentially drive transcription in early stage embryos prior to the heart stage, but expression in late stage and maturing embryos is also suitable. Embryo-preferential promoters that can be used as described herein include the barley lipid transfer protein (Ltp1) promoter (*Plant Cell Rep* 20:647-654 (2001)), YP0097, YP0107, YP0088, YP0143, YP0156, PT0650, PT0695, PT0723, PT0838, PT0879, and PT0740.

Promoters active in photosynthetic tissue confer transcription in green tissues such as leaves and stems and can be used as described herein. Suitable examples include those promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104:997-1006 (1994)), the cab1R promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcb1*2 promoter (Cerdan et al., *Plant Mol. Biol.,* 33:245-255 (1997)), the *Arabidopsis thaliana* SUC2 sucrose-H+ symporter promoter (Truernit et al., *Planta,* 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

Examples of promoters that have high or preferential activity in vascular bundles that can be used as described herein include YP0087, YP0093, YP0108, YP0022, and YP0080. Other vascular tissue-preferential promoters include the glycine-rich cell wall protein GRP 1.8 promoter (Keller and Baumgartner, *Plant Cell,* 3(10):1051-1061 (1991)), the Commelina yellow mottle virus (CoYMV) promoter (Medberry et al., *Plant Cell,* 4(2):185-192 (1992)), and the rice tungro bacilliform virus (RTBV) promoter (Dai et al., *Proc. Natl. Acad. Sci. USA,* 101(2):687-692 (2004)).

Inducible promoters that confer transcription in response to external stimuli such as chemical agents or environmental stimuli can be used as described herein. For example, inducible promoters can confer transcription in response to hormones such as giberellic acid or ethylene, or in response to light or drought. Examples of drought-inducible promoters that can be used as described herein include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters that can be used as described herein include PT0863, PT0829, PT0665, and PT0886. Examples of shade-inducible promoters that can be used as described herein include PR0924 and PT0678. An example of a promoter induced by salt is rd29A. See Kasuga et al. *Nature Biotech,* 17:287-291 (1999).

A basal promoter that can be used as described herein can have a minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

Other classes of promoters that can be used as described herein include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications.

A 5' UTR can be included in a nucleic acid molecule, vector, or construct provided herein. A 5' UTR is transcribed, but is not translated, and can lie between the start site of the transcript and the translation initiation codon and may include the +1 nucleotide.

It will be understood that more than one regulatory region may be present in a nucleic acid molecule, vector, or construct provided herein, e.g., introns, enhancers, upstream activation regions, transcription terminators, and inducible elements. Thus, for example, more than one regulatory region can be operably linked to the sequence of a polynucleotide encoding a polypeptide.

Regulatory regions, such as promoters for endogenous genes, can be obtained by chemical synthesis or by subcloning from a genomic DNA that includes such a regulatory region. A nucleic acid comprising such a regulatory region also can include flanking sequences that contain restriction enzyme sites that facilitate subsequent manipulation.

Transgenic Plants, Plant Cells, and Plant Seeds

This document also provides plant cells (e.g., transgenic plant cells), plants (e.g., transgenic plants), and plant seeds (e.g., transgenic plant seeds) having a nucleic acid sequence that encodes a polypeptide operably linked to a transcription terminator provided herein. As described herein, the nucleic acid sequence encoding a polypeptide can be heterologous with respect to the transcription terminator. In some cases, the plant cells (e.g., transgenic plant cells), plants (e.g., transgenic plants), or plant seeds (e.g., transgenic plant seeds) provided herein can include at least one nucleic acid molecule, vector, or construct provided herein.

A plant or plant cell can be transformed by having a construct integrated into its genome, i.e., can be stably transformed. Stably transformed cells can retain the introduced nucleic acid molecule, vector, or construct with each cell division. A plant or plant cell also can be transiently transformed such that the nucleic acid molecule, vector, or construct is not integrated into its genome. Transiently transformed cells can lose all or some portion of the introduced nucleic acid molecule, vector, or construct with each cell division such that the introduced nucleic acid molecule, vector, or construct cannot be detected in daughter cells after a sufficient number of cell divisions. Both transiently transformed and stably transformed transgenic plants and plant cells can be made and used as described herein.

Transgenic plant cells described herein can constitute part or all of a whole plant. Such plants can be grown in a manner suitable for the species under consideration, either in a growth chamber, a greenhouse, or a field. Transgenic plants can be bred as desired for a particular purpose, e.g., to introduce a nucleic acid molecule, vector, or construct provided herein into other lines, to transfer a nucleic acid molecule, vector, or construct provided herein to other species, or for further selection of other desirable traits. Alternatively, transgenic plants can be propagated vegetatively for those species amenable to such techniques. As described herein, a transgenic plant also refers to progeny of an initial transgenic plant provided the progeny inherits the transgene. Seeds produced by a transgenic plant can be grown and then selfed (or outcrossed and selfed) to obtain seeds homozygous for a nucleic acid molecule, vector, or construct provided herein.

Transgenic plants can be grown in suspension culture, or tissue or organ culture. Solid and/or liquid tissue culture techniques can be used as described herein or as known in the art. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. Examples of solid a medium that can be used as described herein include Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used as described herein, a reporter nucleic acid sequence encoding a reporter polypeptide having a reporter activity can be included in the transformation procedure, and an assay for reporter activity or expression can be performed at a suitable time after transformation. A suitable time for conducting the assay can be about 1-21 days after transformation, e.g., about 1-14 days, about 1-7 days, or about 1-3 days. Transient assays can be used as described herein for rapid analysis in different species, or to confirm expression of a polypeptide (e.g., a heterologous polypeptide) whose expression has not previously been confirmed in particular recipient cells.

Techniques for introducing nucleic acids molecules, constructs, or vectors into monocotyledonous and dicotyledonous plants are known in the art, and examples that can be used as described herein include, without limitation, *Agrobacterium*-mediated transformation, viral vector-mediated transformation, electroporation, and particle gun transformation, e.g., U.S. Pat. Nos. 5,538,880; 5,204,253; 6,329,571 and 6,013,863. If a cell or cultured tissue is used as the recipient tissue for transformation as described herein, plants can be regenerated from transformed cultures if desired, by techniques known to those skilled in the art.

A population of transgenic plants can be screened and/or selected for those members of the population that have a trait or phenotype conferred by expression of the transgene. For example, a population of progeny of a single transformation event can be screened for those plants having a desired level of expression of a polypeptide or nucleic acid. Physical and biochemical methods can be used to identify expression levels. Examples that can be used include Southern analysis or PCR amplification for detecting of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques described herein are known in the art. As an alternative, a population of plants comprising independent transformation events can be screened for those plants having a desired trait, such as a modulated level of a nucleic acid or polypeptide. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in the expression of a transgene relative to a control plant that lacks the transgene. Selected or screened transgenic plants described herein can have an altered phenotype as compared to a corresponding control plant.

The nucleic acid molecules, vectors, and constructs described herein can be used to transform a number of monocotyledonous and dicotyledonous plants and plant cell systems. Examples of monocotyledonous and dicotyledonous plants that can be used as described herein include, without limitation, the following plants: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Examples of suitable plants that can be used as described herein include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Examples of suitable plants that can be used as described herein also include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), *Salix* spp. (willow), *Eucalyptus* spp. (eucalyptus), *Triticosecale* (*triticum*—wheat×rye) and bamboo.

Examples of suitable plants that can be used as described herein also include *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), *Beta vulgaris* (sugarbeet), *Manihot esculenta* (cassava), *Lycopersicon esculentum* (tomato), *Lactuca sativa* (lettuce), *Musa paradisiaca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Examples of suitable plants that can be used as described herein also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum califomica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii*, and *Tanacetum parthenium*.

Examples of suitable plants that can be used as described herein also include *Parthenium argentatum* (guayule), *Hevea* spp. (rubber), *Mentha spicata* (mint), *Mentha piperita* (mint), *Bixa orellana*, and *Alstroemeria* spp.

Examples of suitable plants that can be used as described herein also include *Rosa* spp. (rose), *Dianthus caryophyllus* (carnation), *Petunia* spp. (petunia), *Poinsettia pulcherrima* (poinsettia), *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass), and *Phleum pratense* (timothy).

In some cases, a suitable species that can be used as described herein includes a wild, weedy, or cultivated *Pennisetum* species including, without limitation, *Pennisetum alopecuroides, Pennisetum arnhemicum, Pennisetum caffrum, Pennisetum clandestinum, Pennisetum divisum, Pennisetum glaucum, Pennisetum latifolium, Pennisetum macrostachyum, Pennisetum macrourum, Pennisetum orientale, Pennisetum pedicellatum, Pennisetum polystachion, Pennisetum polystachion* ssp. *Setosum, Pennisetum purpureum, Pennisetum setaceum, Pennisetum subangustum, Pennisetum typhoides, Pennisetum villosum*, or hybrids thereof (e.g., *Pennisetum purpureum*×*Pennisetum typhoidum*).

In some cases, a suitable species that can be used as described herein includes a wild, weedy, or cultivated *Miscanthus* species and/or variety including, without limitation, *Miscanthus*×*giganteus, Miscanthus sinensis, Miscanthus*× *ogiformis, Miscanthus floridulus, Miscanthus transmorrisonensis, Miscanthus oligostachyus, Miscanthus nepalensis, Miscanthus sacchariflorus, Miscanthus*×*giganteus* 'Amuri', *Miscanthus*×*giganteus* 'Nagara', *Miscanthus*×*giganteus* 'Illinois', *Miscanthus sinensis* var. 'Goliath', *Miscanthus sinensis* var. 'Roland', *Miscanthus sinensis* var. 'Africa', *Miscanthus sinensis* var. 'Fern Osten', *Miscanthus sinensis* var. *gracillimus, Miscanthus sinensis* var. *variegates, Miscanthus sinensis* var. *purpurascens, Miscanthus sinensis* var. 'Malepartus', *Miscanthus sacchariflorus* var. 'Robusta', *Miscanthus sinensis* var. 'Silberfedher' (aka. Silver Feather), *Miscanthus transmorrisonensis, Miscanthus condensatus, Miscanthus yakushimanum, Miscanthus* var. 'Alexander', *Miscanthus* var. 'Adagio', *Miscanthus* var. 'Autumn Light', *Miscanthus* var. 'Cabaret', *Miscanthus* var. 'Condensatus', *Miscanthus* var. 'Cosmopolitan', *Miscanthus* var. 'Dixieland', *Miscanthus* var. 'Gilded Tower' (U.S. Patent No. PP14,743), *Miscanthus* var. 'Gold Bar' (U.S. Patent No. PP15,193), *Miscanthus* var. 'Gracillimus', *Miscanthus* var. 'Graziella', *Miscanthus* var. 'Grosse Fontaine', *Miscanthus* var. 'Hinjo aka Little Nicky'™, *Miscanthus* var. 'Juli', *Miscanthus* var. 'Kaskade', *Miscanthus* var. 'Kirk Alexander', *Miscanthus* var. 'Kleine Fontaine', *Miscanthus* var. 'Kleine Silberspinne' (aka. 'Little Silver Spider'), *Miscanthus* var. 'Little Kitten', *Miscanthus* var. 'Little Zebra' (U.S. Patent No. PP13,008), *Miscanthus* var. 'Lottum', *Miscanthus* var. 'Malepartus', *Miscanthus* var. 'Morning Light', *Miscanthus* var. 'Mysterious Maiden' (U.S. Patent No. PP16,176), *Miscanthus* var. 'Nippon', *Miscanthus* var. 'November Sunset', *Miscanthus* var. 'Parachute', *Miscanthus* var. 'Positano', *Miscanthus* var. 'Puenktchen'(aka 'Little Dot'), *Miscanthus* var. 'Rigoletto', *Miscanthus* var. 'Sarabande', *Miscanthus* var. 'Silberpfeil' (aka. Silver Arrow), *Miscanthus* var. 'Silverstripe', *Miscanthus* var. 'Super Stripe' (U.S. Patent No. PP18,161), *Miscanthus* var. 'Strictus', or *Miscanthus* var. 'Zebrinus'.

In some cases, a suitable species that can be used as described herein includes a wild, weedy, or cultivated sorghum species and/or variety including, without limitation, *Sorghum almum, Sorghum amplum, Sorghum angustum,*

Sorghum arundinaceum, Sorghum bicolor (such as bicolor, guinea, caudatum, kafir, and durra), Sorghum brachypodum, Sorghum bulbosum, Sorghum burmahicum, Sorghum controversum, Sorghum drummondii, Sorghum ecarinatum, Sorghum exstans, Sorghum grande, Sorghum halepense, Sorghum interjectum, Sorghum intrans, Sorghum laxiflorum, Sorghum leiocladum, Sorghum macrospermum, Sorghum matarankense, Sorghum miliaceum, Sorghum nigrum, Sorghum nitidum, Sorghum plumosum, Sorghum propinquum, Sorghum purpureosericeum, Sorghum stipoideum, Sorghum sudanensese, Sorghum timorense, Sorghum trichocladum, Sorghum versicolor, Sorghum virgatum, Sorghum vulgare, or hybrids such as Sorghum×almum, Sorghum×sudangrass or Sorghum×drummondii.

The methods and materials provided herein (e.g., nucleic acid molecules, vectors, or construct having a nucleic acid sequence that encodes a polypeptide operably linked to a transcription terminator) can be used over a broad range of plant species, including species from the dicot genera Brassica, Carthamus, Glycine, Gossypium, Helianthus, Jatropha, Parthenium, Populus, and Ricinus; and the monocot genera Elaeis, Festuca, Hordeum, Lolium, Oryza, Panicum, Pennisetum, Phleum, Poa, Saccharum, Secale, Sorghum, Triticosecale, Triticum, and Zea. In some cases, a plant that can be used as described herein can be a member of the species Panicum virgatum (switchgrass), Sorghum bicolor (sorghum, sudangrass), Miscanthus giganteus (miscanthus), Saccharum sp. (energycane), Populus balsamifera (poplar), Zea mays (corn), Glycine max (soybean), Brassica napus (canola), Triticum aestivum (wheat), Gossypium hirsutum (cotton), Oryza sativa (rice), Helianthus annuus (sunflower), Medicago sativa (alfalfa), Beta vulgaris (sugarbeet), or Pennisetum glaucum (pearl millet).

In certain cases, the nucleic acid molecules, vectors, and constructs described herein can be used to transform a number of monocotyledonous and dicotyledonous plants and plant cell systems, wherein such plants are hybrids of different species or varieties of a specific species (e.g., Saccharum sp.×Miscanthus sp., Sorghum sp.×Miscanthus sp., e.g., Panicum virgatum×Panicum amarum, Panicum virgatum×Panicum amarulum, and Pennisetum purpureum× Pennisetum typhoidum).

A plant that contains a polypeptide with modulated expression levels due to increased or decreased transgene expression can be used as described herein. The phenotype of a transgenic plant in which the expression of a polypeptide has been altered can be evaluated relative to a control plant. As described herein, a plant can "not express" a polypeptide when the plant exhibits less than 10%, e.g., less than 9%, 8%, 7%, 6%, 5%, 4%, 3%, 2%, 1%, 0.5%, 0.1%, 0.01° A, or 0.001%, of the amount of polypeptide or mRNA encoding the polypeptide exhibited by the plant of interest. Expression can be evaluated using methods described herein including, for example, RT-PCR, Northern blots, S1 RNase protection, primer extensions, Western blots, protein gel electrophoresis, immunoprecipitation, enzyme-linked immunoassays, chip assays, and mass spectrometry. If a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

Articles of Manufacture

This document also provides a plant seed that can be incorporated into a plant seed composition containing a plurality of $F_1$ hybrid sterile transgenic seeds. The proportion of such seeds in the composition can be from 70% to 100%, e.g., 90%, 91%, 92%, 93%, 94%, 95%, 96%, 97%, 98%, or 99% to 100%. The remaining seeds in the composition can be seeds of one of the parents of the $F_1$, and the proportion of parent seeds can be less than 5%, e.g., 0% to 0.5%, 1%, 2%, or 4%. The proportion of seeds in the composition can be measured as the number of seeds of a particular type divided by the total number of seeds in the composition. When large quantities of a seed composition are formulated, or when the same composition is formulated repeatedly, there can be some variation in the proportion of each type observed in a sample of the composition, due to sampling error. In some cases, such sampling error can typically be about ±5%.

Seeds can be conditioned and bagged in packaging material by means known in the art to form an article of manufacture. Such a bag of seed preferably has a package label accompanying the bag, e.g., a tag or label secured to the packaging material, a label printed on the packaging material or a label inserted within the bag. The package label can indicate that the seeds therein are, for example, $F_1$ hybrid sterile transgenic seeds.

The invention will be further described in the following examples, which do not limit the scope of the invention described in the claims.

EXAMPLES

Example 1

Identifying Transcription Terminators

Arabidopsis thaliana microarray data and genomic sequence information was used to select transcription terminator candidates. Transcription terminators were selected from the 3'UTR of genes that were highly expressed, constitutively active, and functional in all tissues. Transcription terminators were also selected from the 3'UTR of genes that had minimal nucleotide sequence variation in their transcription cleavage sites, and which exhibited minimal leakage of expression on tiling arrays. Additionally, transcription terminators were selected from the 3'UTR of genes whose neighboring genes downstream from the mRNA cleavage site were not highly expressed. The selection of specific sequences was also informed by bioinformatics analysis of sequences surrounding transcript cleavage sites in Arabidopsis thaliana. The following five transcription terminators were among those selected from Arabidopsis thaliana using the above criteria.

A sequence was selected from an area of the genome sequence downstream of the gene encoding metallothionein 2b (At5g02380). This sequence was as set forth in SEQ ID NO:1.

A sequence was selected from an area of the genome downstream of the gene encoding the 60S ribosomal protein L8 (At2g18020). This sequence was as set forth in SEQ ID NO:2.

A sequence was selected from an area of the genome downstream of the gene encoding the small subunit of ribulose-bisphosphate carboxylase (At1g67090). This sequence was as set forth in SEQ ID NO:3.

A sequence was selected from an area of the genome downstream of the gene encoding the cytochrome b6f complex subunit (At2g26500). This sequence was as set forth in SEQ ID NO:4.

A sequence was selected from an area of the genome downstream of the gene encoding elongation factor 1 alpha (At1g07930). This sequence was as set forth in SEQ ID NO:5.

Example 2

Assessing Effectiveness of Transcription Terminators

A vector system was used to assess transcription terminators for the ability to terminate transcription in vivo of a heterologous nucleic acid reporter (e.g., GFP) expressed under the control of a promoter (FIG. 1). The transcription terminator was considered efficient or "tight" if termination and polyadenylation occurred within the transcription terminator sequence. The transcription terminator was considered inefficient or "leaky" if termination and polyadenylation occurred outside the transcription termination sequence (i.e., within the NOS transcription terminator sequence).

Plants were transformed with vectors having candidate transcription terminators, and total RNA was isolated from leaves of transformed plants and was treated with DNase I. Total RNA was then subjected to RT-PCR amplification using the P1 and P2 (Oligo-dT) primers indicated in FIG. 1. The PCR products were cloned into a transfer vector (e.g., pCR II) and transformed into E. coli. The PCR product in each clone was then sequenced with vector primers flanking the insert site. All RNA transcripts polyadenylated within either the transcription terminator being expressed or within NOS terminator were amplified by RT-PCR at similar efficiencies.

The results of the analysis of the transcription terminators having the sequence set forth in SEQ ID NOs:1-5 are presented in Tables 1-5, respectively. The PolyA site nucleotide number corresponds to the location within each respective transcription terminator where polyadenylation occurred (3' of the indicated nucleotide at that position). The number of transcripts having a PolyA site at a particular location when expressed in Arabidopsis and/or rice cells were determined

TABLE 1

Transcription terminator having sequence set forth in SEQ ID NO: 1.

| PolyA site nucleotide number of SEQ ID NO: 1 | Arabidopsis | Rice |
|---|---|---|
| 57 | | 1 |
| 60 | | 1 |
| 63 | | 1 |
| 64 | | 2 |
| 66 | 1 | |
| 101 | | 1 |
| 111 | | 1 |
| 117 | | 1 |
| 119 | 1 | 1 |
| 118 | 1 | |
| 120 | | 1 |
| 121 | 4 | 7 |
| 135 | 2 | 3 |
| 141 | | 1 |
| 153 | 1 | |
| 155 | 3 | 2 |
| 159 | 41 | 97 |
| 164 | | 1 |
| 168 | | 1 |
| 172 | 1 | 1 |

TABLE 1-continued

Transcription terminator having sequence set forth in SEQ ID NO: 1.

| PolyA site nucleotide number of SEQ ID NO: 1 | Arabidopsis | Rice |
|---|---|---|
| 173 | | 1 |
| 174 | 3 | |
| 177 | 2 | |
| 179 | 3 | 12 |
| 184 | | 8 |
| 187 | | 2 |
| 189 | | 2 |
| 192 | | 2 |
| 195 | 3 | 14 |
| 203 | 1 | 1 |
| 206 | | 8 |
| 208 | 2 | |
| 216 | | |

TABLE 2

Transcription terminator having sequence set forth in SEQ ID NO: 2.

| PolyA site nucleotide number of SEQ ID NO: 2 | Arabidopsis | Rice |
|---|---|---|
| 25 | | 2 |
| 26 | | 1 |
| 28 | | 1 |
| 29 | | 1 |
| 34 | | 1 |
| 35 | | 2 |
| 37 | | 1 |
| 45 | | 1 |
| 65 | | 1 |
| 93 | | 1 |
| 108 | 35 | 64 |
| 110 | 6 | |
| 115 | 1 | |
| 117 | 3 | |
| 118 | | 2 |
| 128 | 7 | 34 |
| 138 | | 4 |
| 142 | | 1 |
| 151 | | 2 |
| 175 | 2 | |
| 180 | 4 | 1 |
| 182 | 4 | 3 |
| 213 | 3 | |
| 222 | | 1 |

TABLE 3

Transcription terminator having sequence set forth in SEQ ID NO: 3.

| PolyA site nucleotide number of SEQ ID NO: 3 | Arabidopsis |
|---|---|
| 132 | 1 |
| 136 | 3 |
| 150 | 16 |
| 162 | 4 |
| 180 | 7 |
| 190 | 3 |
| 198 | 2 |

TABLE 4

Transcription terminator having sequence set forth in SEQ ID NO: 4.

| PolyA site nucleotide number of SEQ ID NO: 4 | Arabidopsis |
|---|---|
| 84 | 1 |
| 88 | 1 |
| 106 | 5 |
| 123 | 6 |
| 133 | 5 |
| 136 | 2 |
| 140 | 1 |
| 153 | 1 |
| 161 | 1 |
| within NOS terminator | 1 |

TABLE 5

Transcription terminator having sequence set forth in SEQ ID NO: 5.

| PolyA site nucleotide number of SEQ ID NO: 5 | Rice |
|---|---|
| 118 | 1 |
| 120 | 2 |
| 123 | 2 |
| 134 | 1 |
| 136 | 2 |
| 139 | 57 |
| 141 | 4 |
| 144 | 1 |
| 149 | 1 |
| 151 | 1 |

The results provided herein demonstrate that the transcription terminators having the sequence set forth in SEQ ID NO:1, 2, 3, 4, and 5 have the ability to terminate transcription effectively in vivo.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A plant cell comprising a nucleotide sequence encoding a polypeptide operably linked to a transcription terminator, wherein said nucleotide sequence is heterologous to said transcription terminator, and wherein said transcription terminator comprises a nucleotide sequence having at least 99% identity to the sequence set forth in SEQ ID NO:2.

2. The plant cell of claim 1, wherein said plant cell is a canola, corn, cotton, *miscanthus*, rice, rye, sorghum, soybean, sugar beet, sunflower, switchgrass, or wheat plant cell.

3. The plant cell of claim 1, wherein said transcription terminator comprises the nucleotide sequence set forth in SEQ ID NO:2.

4. The plant cell of claim 1, wherein said nucleotide sequence and said transcription terminator are located on a nucleic acid molecule not integrated into the genome of said plant cell.

5. The plant cell of claim 1, wherein said nucleotide sequence and said transcription terminator are located within the genome of said plant cell.

6. A plant comprising a plant cell comprising a nucleotide sequence encoding a polypeptide operably linked to a transcription terminator, wherein said nucleotide sequence is heterologous to said transcription terminator, and wherein said transcription terminator comprises a nucleotide sequence having at least 99% identity to the sequence set forth in SEQ ID NO:2.

7. The plant of claim 6, wherein said plant is a canola, corn, cotton, *miscanthus*, rice, rye, sorghum, soybean, sugar beet, sunflower, switchgrass, or wheat plant.

8. The plant of claim 6, wherein said transcription terminator comprises the nucleotide sequence set forth in SEQ ID NO:2.

9. A seed comprising a nucleotide sequence encoding a polypeptide operably linked to a transcription terminator, wherein said nucleotide sequence is heterologous to said transcription terminator, and wherein said transcription terminator comprises a nucleotide sequence having at least 99% identity to the sequence set forth in SEQ ID NO:2.

10. The seed of claim 9, wherein said seed is a canola, corn, cotton, *miscanthus*, rice, rye, sorghum, soybean, sugar beet, sunflower, switchgrass, or wheat seed.

11. The seed of claim 9, wherein said transcription terminator comprises the nucleotide sequence set forth in SEQ ID NO:2.

12. A vector comprising a nucleic acid molecule comprising a nucleotide sequence encoding a polypeptide operably linked to a transcription terminator, wherein said nucleotide sequence is heterologous to said transcription terminator, and wherein said transcription terminator comprises a nucleotide sequence having at least 99% identity to the sequence set forth in SEQ ID NO:2.

13. The vector of claim 12, wherein said transcription terminator comprises the sequence set forth in SEQ ID NO:2.

\* \* \* \* \*